United States Patent [19]

Kendall

[11] Plant 4,872

[45] Aug. 3, 1982

[54] AVOCADO TREE

[75] Inventor: Harold E. Kendall, Goulds, Fla.

[73] Assignee: Kendall Brothers Trust, Goulds, Fla. ; G. David Parrish, Harold E. Kendall, Jr., Peter H. J. Kendall, Trustees

[21] Appl. No.: 224,827

[22] Filed: Jan. 13, 1981

[51] Int. Cl.[3] ..... A01H 5/03

[52] U.S. Cl. ..... Plt./44

[58] Field of Search ..... Plt./44

*Primary Examiner*—Robert E. Bagwill

*Attorney, Agent, or Firm*—Harvey B. Jacobson

[57] ABSTRACT

An avocado tree characterized by its small size fruit which is ready for picking in South Florida from September to early or mid October, at a time when there are few good quality small fruit maturing in Florida.

2 Drawing Figures

This discovery relates to a new and distinct cultivar of avocado fruit tree which has desirable characteristics. This cultivar has been named 'Christina'.

The original 'Christina' tree was found in the "South Graham" grove of the Kendall Foods Corporation in Goulds, South Dade County, Fla., and has been propagated. The 'Christina' is of unknown parents but botanically resembles a hybrid between the Guatemalan and Antillian avocado races.

The 'Christina' cultivar is very desirable since it is a small size fruit ready for picking in South Florida from September to early or mid October, at a time when there are few good quality small fruit maturing in Florida. The 'Christina' early season coincides with the 'Lisa' late picking season, and then extends to mid October, thus filling the market need for a small fruit during its season.

Figure 1:
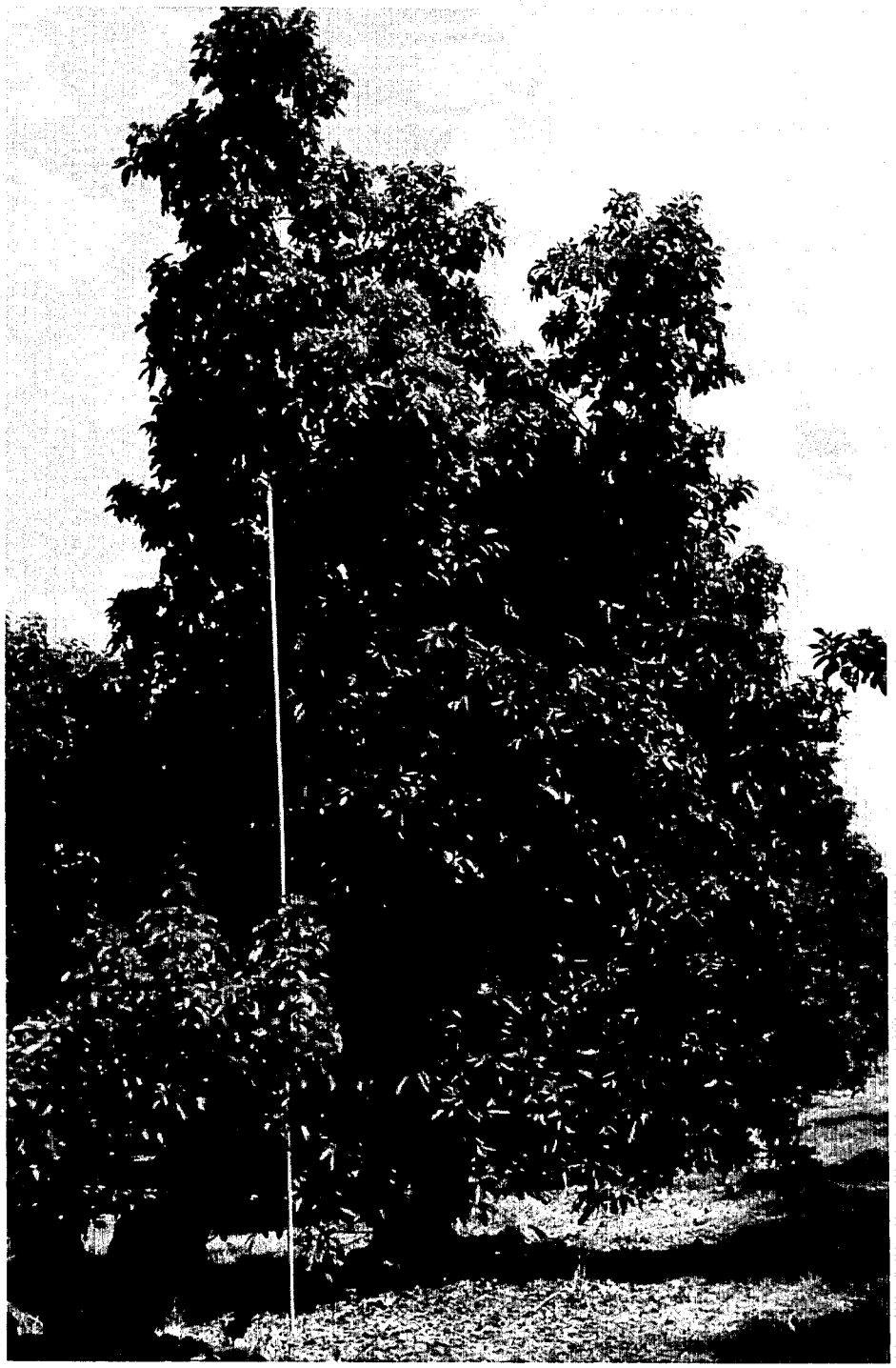
Figure 2:
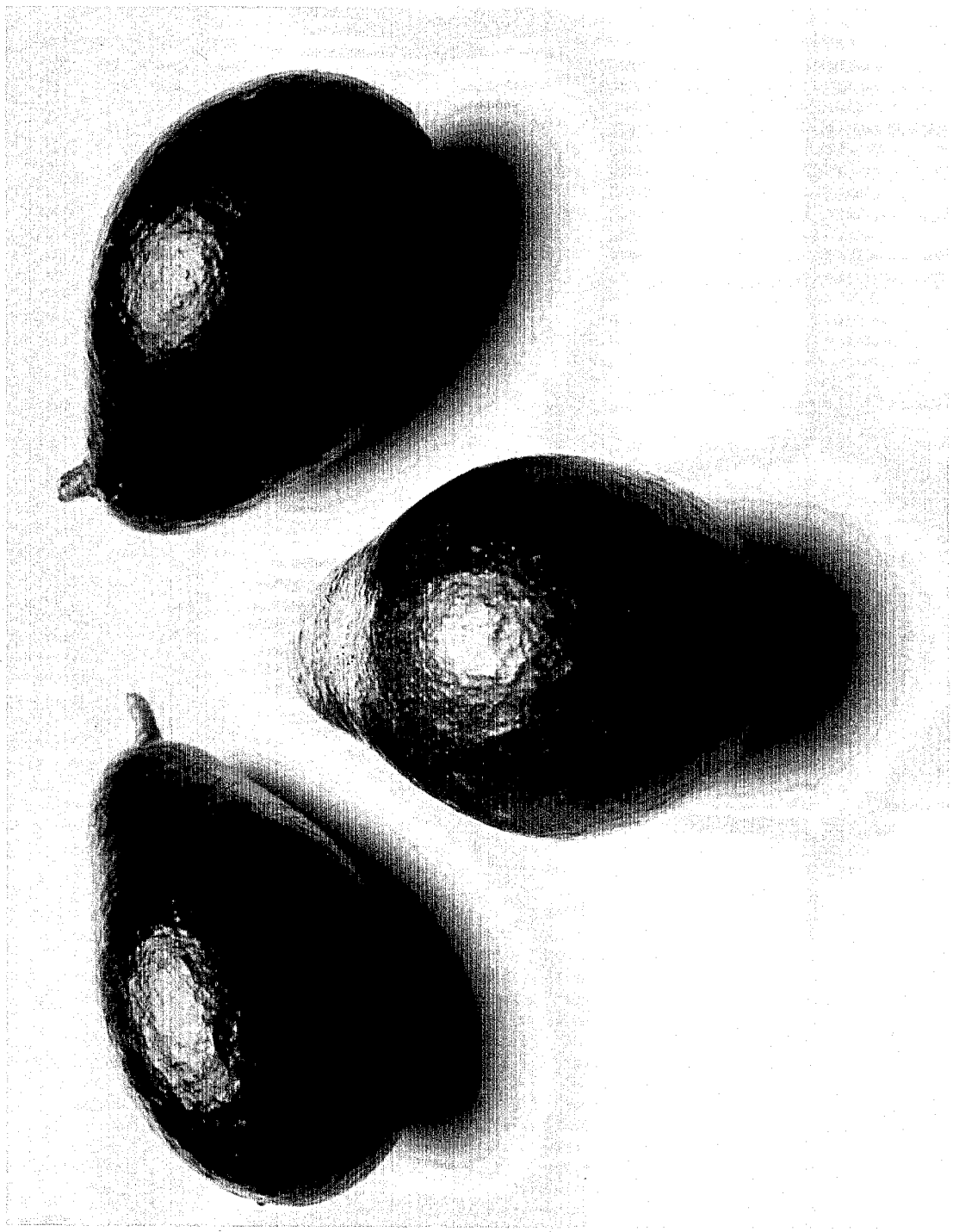

The accompanying photographs show the mature tree (FIG. 1) and the mature fruit (FIG. 2).

A detailed description of the 'Christina' cultivar follows:

SCIENTIFIC AND CULTIVAR NAME

*Persea americana* cv. 'Christina'

RACE

Probably a Guatemalan × Antillian hybrid.

TREE

'Christina' trees are very vigorous and grow erect like the 'Reed' and 'Bacon' cultivars requiring topping several times during the first two or three years after planting in order to get a more spreading type of growth. The green foliage is abundant and shoots have a tendency to hang downward, especially those bearing fruit. Leaves are mostly lanceolate; the edges being smooth and slightly undulating. The upperside of the leaves is smooth, green to dark green and shiny and the underside is less green and dull. Leaf petiole and veins are greenish yellow. Mature trees bear adequately, with indications of some degree of alternate bearing. A large number of the fruit set is in clusters. Cold tolerance has not been determined, though trees under sprinkler irrigation were not damaged by the 1977 freeze. The blooming season in 1979 was from early March to early April and the flowers are B type.

FRUIT

Outside:

The 'Christina' fruit stem attachment is moderately thick and three easily differentiated parts of the peduncle may be observed. First, there is a disc of about 1.02 cm (0.4 inches) in diameter and 0.25 cm (0.1 inches) in thickness at the point of attachment. Then a thinner cylindrical section follows which is about 0.76 to 1.02 cm (0.3 to 0.4 inches) long and 0.51 to 0.76 cm (0.2 to 0.3 inches) in diameter and, finally, a still thinner section of 0.25 to 0.38 cm (0.10 to 1.15 inches) in diameter and several inches long attaches to the shoot.

'Christina' fruits are small and weigh 227 to 398 grams (8 to 14 ounces). Fruits measure 7.26 to 7.34 cm (2.86 to 2.89 inches) in widest area and 11.38 to 11.89 cm (4.48 to 4.68 inches) in length.

Fruits are mostly pyriform but oval fruits and intermediate shapes between these two are common. The short neck is thick, making the fruit very attractive. The skin is green to dark green, slightly leathery and easy to cut. There is not much change in skin color upon softening. It takes 7 to 10 days for the fruit to soften at 21°–24° C. (70°–75° F.). A few brown specks around the neck were observed on the skin of some fruits after softening. The skin is free of corky lenticels but it is slightly susceptible to scab.

Inside:

The skin of 'Christina' fruit is slightly leathery and easy to cut. Flesh color is creamy-yellow around the seed and green to light green near the skin. The mean flesh thickness from seed to stem end is 4.47 cm (1.76 inches); that from seed to stylar end is 2.41 cm (0.95 inches); and that from seed to equator edge is 1.42 cm (0.56 inches). The flesh green area or aureola around the periphery of the fruit varies from 0.64 to 1.60 cm (0.25 to 0.63 inches) in thickness.

The seed is medium to small in size and it is held tightly against the flesh. The seed coat adheres to the seed thus leaving a clean cavity upon seed removal. Seed weight varies from 42.60 to 78.10 grams (1.50 to 2.75 ounces) and it represents from 15 to 20% of the total weight of the fruit. Mean seed length by width dimensions are 4.57 by 4.60 cm (1.80 by 1.81 inches) respectively.

Quality:

'Christina' fruit flavor is very good, nutty and mealy. Fruit softening is normal with an absence of hard areas in the flesh. A small number of light brown fibers may be present in a few fruits in the flesh at the stylar end area but in the majority of the fruits fibers are absent.

TABLE 1

COMPARISON WITH OTHER CULTIVARS

| Cultivar | Picking Season | Size Ounces | Size Grams | Flower Type | Appearance |
|---|---|---|---|---|---|
| 'Christina' | September–October | 8–14 | 227–398 | B | Small, pyriform to slightly oval, slightly leathery, green to dark green. |
| 'Lisa' | August–September | 9–14 | 256–398 | B | Samll oval-round to slightly pyriform, smooth, green to dark green. |
| 'Miguel' | August–September | 18–22 | 511–625 | B | Large, oval with clef dark green, slightly leathery. |
| 'Waldin' | September–October | 12.16 | 341–454 | A | Medium, oval, smooth, light green. |

TABLE 1-continued

COMPARISON WITH OTHER CULTIVARS

Having thus described my discovery, I claim:

1. A new and distinct cultivar of avocado tree as described and shown.

* * * * *